United States Patent [19]

Peck

[11] Patent Number: 5,698,593
[45] Date of Patent: Dec. 16, 1997

[54] METHOD FOR TREATING ACNE

[75] Inventor: Gary L. Peck, Silver Spring, Md.

[73] Assignee: The United States of America as represented by the Department of Health and Human Services, Washington, D.C.

[21] Appl. No.: 47,007

[22] Filed: Apr. 15, 1993

Related U.S. Application Data

[63] Continuation of Ser. No. 735,113, Jul. 24, 1991, abandoned, which is a continuation of Ser. No. 186,260, Apr. 26, 1988, abandoned.

[51] Int. Cl.$^6$ .......................... A61K 31/12; A61K 31/20
[52] U.S. Cl. .................. 514/557; 514/559; 514/859
[58] Field of Search .......................... 514/559, 725, 514/859, 152, 172, 182, 602

[56] References Cited

U.S. PATENT DOCUMENTS

| | | | |
|---|---|---|---|
| 3,729,568 | 4/1973 | Kligman | 424/318 |
| 3,882,244 | 5/1975 | Lee | 424/318 |
| 3,932,665 | 1/1976 | Van Scott et al. | 422/333 |
| 3,934,028 | 1/1976 | Lee | 424/318 |
| 4,322,438 | 3/1982 | Peck | 514/557 |
| 4,487,782 | 12/1984 | Nezick | 424/317 |
| 4,545,977 | 10/1985 | Gaull | 514/578 |
| 4,677,120 | 6/1987 | Parish et al. | 514/544 |

FOREIGN PATENT DOCUMENTS 2156676  10/1985  United Kingdom.

OTHER PUBLICATIONS

Windholz et al., *The Merck Index*, 10th Ed. p. 1315, abstract No. 9021 (Tetracycline).
Sporn et al., The Retnoids, 1984, vol. 1, pp. 393–412.
Perry et al., "Isotretinoin: New therapy for severe acne", Clinical Pharmacy, Jan.–Feb. 1983, pp. 12–19.
Orfanos et al, "The Retnoids", Drugs: 1987, pp. 469–472.
Cunliffe et al, "Isotretinoin An Explanation for Its Long–Term Benefit", Dermatological, 1987, pp. 133–137.
Cunliffe et al, "Isotretinoin and Acne: A Long–Term Study", Dermatology Branch National Cancer Institutes, 1991, pp. 274–280.

*Primary Examiner*—Kevin E. Weddington
*Attorney, Agent, or Firm*—Laurence J. Hyman; Office of Technology Transfer, NIH

[57] ABSTRACT

Nodulocystic and conglobate acne in humans can be alleviated by the oral administration of 13-cis-retinoic acid or a derivative thereof. The active ingredient is administered in a dosage of from about 1.5 to about 3 mg/kg of body weight per day for a period of from about two to about four weeks.

11 Claims, No Drawings

METHOD FOR TREATING ACNE

This is a continuation of application Ser. No. 07/735,113, filed on Jul. 24, 1991, now abandoned which is a continuation of Ser. No. 07/186,260, filed Apr. 26, 1988, now abandoned.

FIELD OF THE INVENTION

The present invention relates to an improved method of treating acne with 13-cis-retinoic acid and appropriate derivatives thereof.

BACKGROUND OF THE INVENTION

Retinol (Vitamin A) and retinoic acid (vitamin A acid), its isomers, and certain of its analogs are known to have beneficial effects in the treatment of acne and keratinizing skin disorders.

Acne affects large patient populations, and is a common inflammatory skin disorder which usually localizes on the face. Fortunately, the disease usually disappears, and in the interval of months or years between onset and resolution, therapy, although not curative, can satisfactorily suppress the disease in the majority of patients.

A small number of acne patients with severe disease show little or no response to intensive therapeutic efforts, including the use of high doses of oral tetracycline, dapsone, prednisone, and in women, estrogen. In many of these severe cases, drugs afford only a modest degree of control, while the side effects of these agents may severely restrict their usefulness.

Patients with nodulocystic acne suffer from large inflammatory suppurative nodules and cysts appearing on the face and, frequently, on the back and chest. In addition to their appearance, the lesions are tender and often purulently exudative and hemorrhagic. Disfiguring scars are frequently inevitable.

Therapies for acne in patients who have failed to respond adequately to treatment with antibiotics and hormonal therapy have previously been reported. These therapies involve local and systemic administration of vitamin A compounds, collectively known as retinoids. Topical application of all-trans retinoic acid has been tried with some success, particularly against comedones or blackheads, but this condition frequently returns when the treatment is withdrawn. Additionally, retinoic acid applied topically can be highly irritating, and its use can be painful for the patient, depending upon the concentration used and the frequency of application.

A number of side effects complicate the administration of large doses of vitamin A. Among the many symptoms of hypervitaminosis A are weight loss, desquamation of the skin, hair loss, irritation of the oral and pharyngeal mucosa, and nose bleeds, headaches, bone pain, liver toxicity due to storage of vitamin A in the liver, papilledema, pseudotumor cerebri, and demineralization and periosteal thickening of bones. Because of these and other side effects, oral treatment with vitamin A and all-trans retinoic acid, which produces similar side effects, is rarely recommended for dermatopathic conditions.

The process of treating acne vulgaris topically using retinal, the aldehyde form of vitamin A, is disclosed in U.S. Pat. No. 3,932,665. The aldehyde form, unlike the acid form of vitamin A, exerts its therapeutic effect without producing irritation, inflammation, erythema, or peeling of the skin. This patent also discloses the topical use of 13-cis-retinal in the treatment of acne vulgaris.

A method for treating acne with C-20 and C-22 vinylogs of desmethyl retinoic acid is disclosed in U.S. Pat. No. 3,882,244. These vinylogs as disclosed are applied topically to the site of the acne infection as a solution, ointment, or powder.

One method of use of 13-cis-retinoic acid provides a dosage of 1 mg/kg/day for five months. The problem with this dosage schedule is that any fetus carried during the five months administration and for a month after treatment may suffer from teratogenic effects of the drug. In addition, the patient may suffer the effects of acute toxicity, including arthralgias and myalgias. Harmful changes in blood chemistry, especially hyperlipidemia, may occur.

In "Investigational Drug Brochure RO4-3780," printed by Hoffman-LaRoche, Inc., there appear several general statements indicating that all-trans retinoic acid had been used for the oral treatment of acne, and that 13-cis-retinoic acid had proved to be less toxic than all-trans retinoic acid in animal experiments. However, dosages were not discussed.

Belgian Patent No. 762,344 also discloses the use of orally administered 13-cis-retinoic acid for the treatment of acne and psoriasis. However, only a general dosage for various vitamin A compounds of from 0.1 mg to 0.5 mg to about 3.0 mg per kg of body weight is disclosed. Moreover, there is no example directed towards the use of 13-cis-retinoic acid or the improved method of administration disclosed herein.

Straumford, in *Northwest Med.* 42: 219–244, 943, reported a systemic usage of large oral doses of retinol, the alcohol form of vitamin A, for a long period of time for the treatment of acne. These results, however, have been disputed, and systemic therapy of acne utilizing retinol has been challenged by other investigators (Anderson et al., *Brit. Med. J.* 2: 294–296, 1963; Lynch et al., *Arch. Derm.* 55: 355, 357, 1947; and Mitchell et al., *Arch. Derm.* 64: 428–434, 1951). However, no mention of the improved method which is the subject of the present application is disclosed.

The treatment of acne vulgaris with retinoic analogs, particularly 11-(2',6',6'-trimethylcyclohex-1'enyl-1-)-5,9-dimethylundeca-2,4,6,8,10-pentenoic acid is disclosed in U.S. Pat. No. 3,934,028. This compound can be used either internally or topically. When taken orally, the daily dosage of this compound is from 20–300 mg taken over a period of from two to eight weeks. However, there is no indication that the compounds lead to remission from the disease after administration of the compound is withdrawn.

An improved method of treating nodulocystic and conglobate acne in humans by oral administration of 13-cis-retinoic acid in amounts and for periods of time which afford an effectively complete remission from the condition even after administration of the compound ceases is disclosed in Peck, U.S. Pat. No. 4,322,438. This improvement, however, involves the use of a high-low oral dosage schedule, which is said to be effective in the treatment of cystic acne, while reducing the toxic effects of the 13-cis-retinoic acid.

Further studies by Jones et al., reported in *The Lancet* (1980), 1048, indicate that a four month course of therapy with oral 13-cis-retinoic acid was begun at a minimum divided dosage of 1.0 mg per kilogram of body weight per day. The dosage was then increased in increments of 0.5 to 1.0 mg/kg/day at intervals of two to four weeks until either an appreciable therapeutic effect or dose-limiting toxicity was observed. There are dose-related side effects associated with the use of 13-cis-retinoic acid, particularly dryness of the skin and mucous membranes. More seriously, 13-cis-retinoic acid, which is marketed as an oral acne drug, can cause serious birth defects. Among other serious short-term effects are increased pressure in the brain (pseudotumor cerebri), clouding of the cornea (cornealppacilies), and inflammation of the intestines (colitis).

The *Handbook of Nonprescription Drugs*, fifth edition, 1977, A.P.A. pub., pp 140, 319, 320, discloses the use of vitamin A and retinoic acid, but not the use of the 13-cis-geometric isomer, in the treatment of acne. However, this disclosure is opposite that of the subject invention, in that it states, "The systemic use of vitamin A for the treatment of acne . . . is not warranted by clinical evidence" at page 140; and, "Treatments that have been abandoned or have not been proved effective include oral vitamin A . . . " at page 320.

Topical administration of retinoic acid for the treatment of acne was reported by Kligman et al. in U.S. Pat. 3,729,568. The effectiveness of this treatment is often associated with a noticeable irritating effect of topically applied retinoic acid.

The treatment of acne vulgaris with retinoic analogs, particularly 11-(2',6',6'-trimethylcyclohex-1'enyl-1')-5,9-dimethylundeca-2,4,6,8,10-pentenoic acid is disclosed in U.S. Pat. No. 3,934,028. This compound can be used either internally or topically. When taken orally, the daily dosage of this compound is from 20–300 mg taken over a period of from two to eight weeks. However, there is no indication that the compounds lead to remission from the disease after administration of the compound is withdrawn.

Although 13-cis-retinoic acid is generally less toxic than all-trans retinoic acid, there are still precautions that must be observed in its use. With oral retinoic acid, headaches, nausea, vomiting, and some of the skin and mucous membrane lesions experienced with hypervitaminosis A have been reported. Because of chemical and pharmacological similarities between 13-cis-retinoic acid, retinoic acid, and retinol, similar adverse reactions occur with 13-cis-retinoic acid, cf. Windhurst et al., *J.A.A.D.* 6: 675–682, 1982.

Other drugs presently used in the treatment of acne include topical benzoyl peroxide, topical tretinoin (all-trans retinoic acid), topical and oral clindamycin, tetracycline, and erythromycin, oral minocycline, and oral estrogen. Benzoyl peroxide is considered to be safe and effective in mild and moderate acne treatment. Tretinoin is effective, but it has the previously mentioned deleterious side effects, as well as accelerating photocarcinogenesis. The antibiotics are reasonably effective, but have side effects such as gastrointestinal problems, including reports of pseudemembranous colitis by clindamycin. Estrogens are sometimes effective in treating acne in females, but the side effects of these hormones may make them undesirable.

Parish et al. in U.S. Pat. No. 4,677,120, disclose the topical administration to mice and the oral administration to hamsters of esters and amides of 13-cis-retinoic acid which may be used for the treatment of acne and skin disorders. These derivatives of 13-cis-retinoic acid may retain the effectiveness of 13-cis-retinoic acid and may be free of the deleterious side effects of 13-cis-retinoic acid.

13-cis-retinoic acid is currently recommended to be used at a dosage of 1 mg/kg/day for five months. The problem with this dosage schedule is that women are at risk of teratogenicity for five months and for one month post treatment. DISH-like changes may be seen on X-rays, cf. Kilcoyne et al., *Invest. Radiol.* 21: 41–44, 1986. Acute toxicities persist for the duration of the therapy, including mucocutaneous, arthralgias, myalgias, laboratory abnormalities, especially hyperlipidemia (triglycerides and cholesterol). In addition to the contraindications for use during or before pregnancy, there is also the expense of medication, laboratory tests, and physicians' office visits, because the patient must be closely monitored during the administration of the medication.

SUMMARY OF THE INVENTION

It is an object of the present invention to overcome the deficiencies of the prior art, such as indicated above.

It is another object of the present invention to provide an improved treatment schedule for acne patients.

It is yet a further object of the present invention to provide an improved treatment schedule for treating acne patients with 13-cis-retinoic acid and its derivatives.

The currently recommended dosage schedule for the treatment of acne with 13-cis-retinoic acid was established sometime prior to September, 1982, when the FDA approved the use of 13-cis-retinoic acid by prescription. The value of this schedule was determined by treating patients with very severe cases of cystic acne who were admitted to experimental protocols testing the efficacy and toxicity of 13-cis-retinoic acid. Because of the demand for this drug prior to release, only the most severely affected patients were admitted into these initial clinical trials.

Currently, patients being treated have much less severe conditions for a variety of reasons. Patients with severe cystic acne who eventually relapse after treatment with 13-cis-retinoic acid still have much less disease than before their initial exposure to the drug, and patients are being treated in earlier stages of the disease. Dermatologists are more familiar with 13-cis-retinoic acid and are more comfortable in prescribing it. It is now commonplace to treat non-cystic acne with 13-cis-retinoic acid if the acne is chronic, antibiotic-resistant, and is associated with scarring. Most of the severe cases of acne have been treated in the past five years and are in long-term remission. Therefore, it is possible and perhaps likely that the currently used schedule is in fact excessive therapy for a portion of acne patients who have less severe, but antibiotic resistant, disease.

According to the present invention, acne can be treated by administering to a patient having mild cystic acne or with scarring non-cystic acne a compound selected from the group consisting of 13-cis-retinoic acid and its derivatives, in an amount of approximately 1.5 to 3 mg/kg/day for a period of from about two to about four weeks. The treatment is then stopped, despite any persistent acne. The patients are then observed for three to four months to determine the need for additional treatment. If minimal acne remains, the short course of treatment may be repeated. If moderate or severe acne is present, then the current recommended method of 1 mg/kg/day for five months may be added.

The method of the present invention substantially reduces the number of patients who must receive the full five-month course of treatment with 13-cis-retinoic acid or its derivatives, and thus reduces the total dose administered to patients. This, of course, reduces the duration of acute toxicity, the risk of teratogenicity, the risk of chronic radiologic toxicity, and the number of laboratory tests and physicians' office visits required to monitor the therapy. This has the beneficial effect of also reducing the expense and inconvenience to the patient.

DETAILED DESCRIPTION OF THE INVENTION

The method of the present invention is particularly useful for treating patients with mild cystic acne or with scarring non-cystic acne of the face. The active ingredients that can be used in this method of treatment include 13-cis-retinoic acid and its derivatives of the formula:

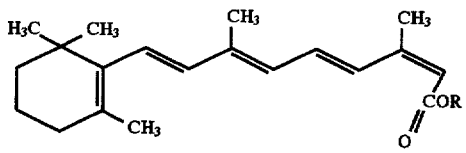

wherein R is any substituent that will not interfere with the efficacy of the compounds in treating acne. Some possible examples of R are as follows:

 (1)

 (2)

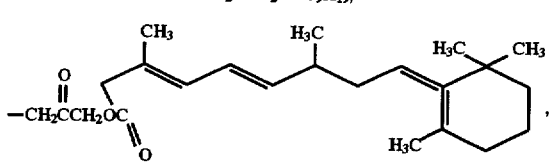 (3)

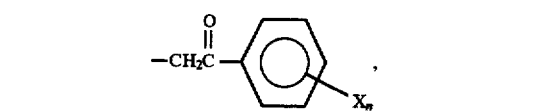 (4)

 (5)

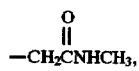 (6)

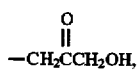 (7)

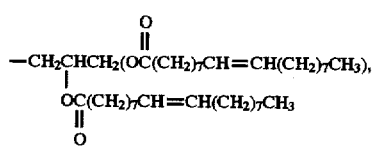 (8)

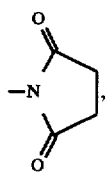 (9)

 (10)

 (11)

 (12)

 (13)

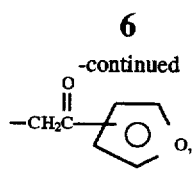 (14)

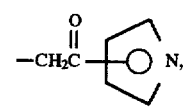 (15)

or

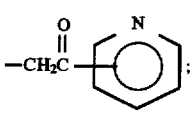

wherein X is —H, —F, —Cl, —Br, —I, —OH, —OR',

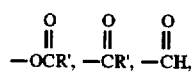

—CN, —NO$_2$, —NH$_2$, —NHR', or —NR'$_2$; wherein n is a number from 1 to 5; wherein R' is a member of the group consisting of lower alkyls ranging from C$_1$ to C$_6$; and wherein R" is a member of the group consisting of

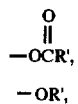

—OR',

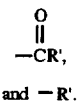

and —R'.

There is no limit to the types of substituents that may be present on the 13-cis-retinoic acid compounds, as long as these substituents do not interfere with the activity of the compounds in treating acne.

To test the efficacy of the improved dosage of the present invention, five patients, four male, one female, with fewer than 15 cysts on the face (mean: 11.6; range, 10–13) prior to treatment were treated with a two-week course using a high dose, 2 mg/kg/day, of 13-cis-retinoic acid.

After two weeks of therapy, there had been a 32.8% decrease in the number of cysts per patient, i.e., from 11.6 to 7.8. Despite this partial response, these patients, who were participating in a three-arm, randomized double-blind study, were given a placebo after the second week's visit for an additional fourteen weeks. Instead of the disease worsening or remaining unchanged from the second week level of activity, the disease improved. At the end of the sixteen week study period, there was an overall 84.5% improvement. Furthermore, after an additional four weeks of observation, the net improvement was 87.9%.

All patients required further therapy with 13-cis-retinoic acid in the future. However, the time to retreatment ranged from 5 to 52 months, with a mean of 23 months. Therefore, patients who had severe, previously treatment-resistant cystic acne were surprisingly able to remain untreated for 23 months after only a two week course of therapy with 13-cis-retinoic acid.

Two of these patients were successfully treated with oral antibiotics prior to eventually relapsing 12 or 24 months later at which time they received a second course of 13-cisretinoic acid therapy. Thus, they had been converted from antibiotic-resistant to antibiotic-responsive after their initial course of 13-cis-retinoic acid. For example, one patient was treated with antibiotics nine months after finishing the first two week course of 13-cis-retinoic acid according to the present invention. This patient was not retreated with 13-cis-retinoic acid until the 21st month following treatment. Similarly, the second patient received antibiotics at the 28th month, and the second course of 13-cis-retinoic acid at the 52nd month.

The treatment regimen of the present invention is particularly effective in the case of patients who have scarring, recalcitrant, non-cystic acne of the face. These milder patients respond even more favorably than the more severely affected patients described above. Even when the patient with milder conditions do not clear completely with the short course of administration, they may be converted to antibiotic-responsive patients who require no further 13-cis-retinoic acid therapy. For the purposes of the present invention, mild cystic acne involves approximately five cysts or fewer, rather than the average of more than 11 cysts per patient in the case of those patients with severe cystic acne as described herein.

The optimum treatment schedule for patients with mild cystic acne or persistent non-cystic acne is a short-term, high-dose schedule of from about 1.5 to about 3 mg/kg/day for at least two and up to four weeks. In the case of pre-menopausal women, treatment can begin on day 1 of the menstrual cycle and end on day 1 of the next menstrual cycle.

There should be a wait of approximately three to four months after therapy before the response is evaluated regarding additional 13-cis-retinoic acid therapy. During this time, conventional therapy, such as oral antibiotics, topical tretinoin, benzoyl peroxide, or antibiotics could be used, although these conventional therapies may not be necessary.

The advantages of the shorter, high-dose therapeutic regimen according to the present invention are as follows:

1. Decreased risk of bone toxicity, which is a function of the total dose received. In the conventional long course of therapy, approximately 12,000 mg of 13-cis-retinoic acid are used for an 80 kg male, whereas, in the short course according to the present invention, only approximately 4800 mg are used for the same patient.

2. Decreased risk of teratogenicity for fertile women, as the short term dosage regimen is only for two weeks or slightly longer rather than for five or six months. Additionally, one wash-out period can be included for fertile women.

3. Increased comfort for the patient, because the acute toxicities, mucocutaneous, myalgias and arthralgias, etc., will be present for only two or four weeks, not for five or six months.

4. Decreased need and expense for laboratory tests, physicians' office visits, and purchase of medication.

Depending upon the patient's response to the short course of therapy according to the present invention, and depending upon the severity of the disease observed at the time of relapse, if any, the second course of therapy with 13-cis-retinoic acid or its derivatives as described above can either be a repeat of the short course of therapy, or can be a longer course of 1 mg/kg/day for five or six months.

While the invention is described above in relation to certain specific embodiments, it will be understood that many variations are possible, and that alternative or additional therapies can be used without departing from the invention. In some cases, such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. In a method of alleviating primarily facial nodulocystic and conglobate acne in humans by the oral administration of a 13-cis-retinoic acid compound selected from the group consisting of 13-cis-retinoic acid and compounds of the formula:

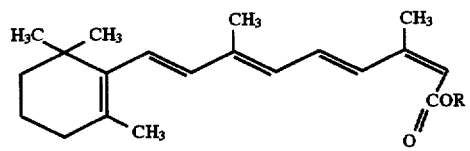

wherein R is selected from the group consisting of:

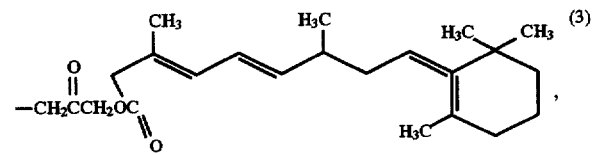

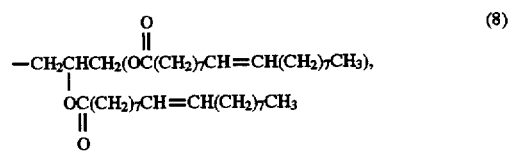

-continued

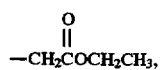
(10)

(11)

(12)

—CHR"$_2$, (13)

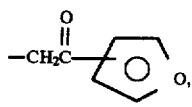 (14)

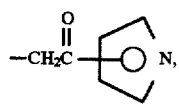

or

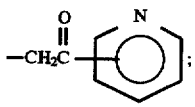

wherein X is —H, —F, —Cl, —Br, —I, —OH, —OR',

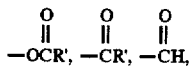

—CN, —NO$_2$, —NH$_2$, —NHR', or —NR'$_2$; wherein n is a number from 1 to 5; wherein R' is a member of the group consisting of lower alkyls ranging from C$_1$ to C$_6$; and wherein R" is a member of the group consisting of

—OR',

and —R'.

and R'in a dosage of from about 1.5 to about 3 mg/kg of body weight per day for a period of from about two to about four weeks, the improvement comprising; then ceasing said administration of the 13-cis-retinoic acid compound despite any persistent acne.

2. The method of claim 1 wherein the treatment is repeated after a wait of at least three months if necessary to achieve a complete therapeutic response, and upon each recurrence of the acne.

3. The method of claim 1 wherein 13-cis-retinoic acid is administered.

4. The method of claim 1 wherein the dosage is about 2 mg/kg of body weight per day for from about two to about four weeks.

5. The method of claim 1, wherein said acne is cystic acne.

6. The method of claim 1, wherein said acne is scarring, non-cystic acne.

7. The method of claim 5, wherein said facial acne comprises 15 or fewer cysts.

8. The method of claim 7, wherein said facial acne is antibiotic-resistant acne.

9. The method of claim 8, wherein said acne further comprises about 10 to about 13 cysts.

10. The method of claim 5, wherein said acne further comprises from about 10 to about 5 cysts.

11. The method of claim 5, wherein said acne is recalcitrant acne comprising about 5 or fewer cysts.

* * * * *